US012788883B2

(12) United States Patent
Drost

(10) Patent No.: US 12,788,883 B2
(45) Date of Patent: Nov. 10, 2026

(54) PROCEDURE-BASED PROGRAMMING FOR INFUSION PUMPS

(71) Applicant: ICU Medical, Inc., Plymouth, MN (US)

(72) Inventor: James B. Drost, Woodbury, MN (US)

(73) Assignee: ICU MEDICAL, INC., San Clemente, CA (US)

( * ) Notice: Subject to any disclaimer, the term of this patent is extended or adjusted under 35 U.S.C. 154(b) by 344 days.

(21) Appl. No.: 18/670,545

(22) Filed: May 21, 2024

(65) Prior Publication Data

US 2024/0390582 A1 Nov. 28, 2024

Related U.S. Application Data

(60) Continuation of application No. 18/150,064, filed on Jan. 4, 2023, now Pat. No. 11,986,628, which is a (Continued)

(51) Int. Cl.
*A61M 5/172* (2006.01)
*A61M 5/14* (2006.01)
(Continued)

(52) U.S. Cl.
CPC .............. *A61M 5/172* (2013.01); *A61M 5/14* (2013.01); *A61M 5/1408* (2013.01); (Continued)

(58) Field of Classification Search
CPC ...... A61M 5/172; A61M 5/14; A61M 5/1408; A61M 5/142; A61M 5/1452;
(Continued)

(56) References Cited

U.S. PATENT DOCUMENTS 4,978,335 A 12/1990 Arthur
5,295,967 A 3/1994 Rondelet et al.
(Continued)

FOREIGN PATENT DOCUMENTS

CN 103920206 A 7/2014
EP 0319268 A2 6/1989
(Continued)

OTHER PUBLICATIONS

Extended European Search Report for European Application No. 24193567.5 dated Mar. 20, 2025, 17 pgs.
(Continued)

*Primary Examiner* — Dung T Ulsh
(74) *Attorney, Agent, or Firm* — Husch Blackwell LLP

(57) ABSTRACT

Methods and systems for configuring a plurality of infusion pumps according to a functional set. A method includes implementing a plurality of infusion pumps, each of the infusion pumps configured to administer medication to a patient, implementing a drug library, the drug library including at least one functional set defining a set of medications, receiving input data related to one of the at least one functional sets, obtaining a particular set of medications from the drug library corresponding to the input data, programming the plurality of infusion pumps according to the set of medications, and infusing the patient with the plurality of infusion pumps.

15 Claims, 9 Drawing Sheets

Related U.S. Application Data division of application No. 15/578,101, filed as application No. PCT/US2016/034007 on May 25, 2016, now Pat. No. 11,571,513.

(60) Provisional application No. 62/170,891, filed on Jun. 4, 2015.

(51) Int. Cl.

| | |
|---|---|
| ***A61M 5/142*** | (2006.01) |
| ***A61M 5/145*** | (2006.01) |
| ***A61M 5/168*** | (2006.01) |
| ***G16H 20/17*** | (2018.01) |
| ***G16H 40/40*** | (2018.01) |
| ***G16H 40/63*** | (2018.01) |
| ***G16H 40/67*** | (2018.01) |
| ***G16H 70/20*** | (2018.01) |
| ***G16H 70/40*** | (2018.01) |

(52) U.S. Cl.

CPC .......... *A61M 5/142* (2013.01); *A61M 5/1452* (2013.01); *A61M 5/16827* (2013.01); *G16H 20/17* (2018.01); *G16H 40/40* (2018.01); *G16H 40/63* (2018.01); *G16H 40/67* (2018.01); *A61M 2005/14208* (2013.01); *A61M 2205/3576* (2013.01); *A61M 2205/502* (2013.01); *A61M 2205/52* (2013.01); *G16H 70/20* (2018.01); *G16H 70/40* (2018.01)

(58) Field of Classification Search

CPC .... A61M 5/16827; A61M 2005/14208; A61M 2205/3576; A61M 2205/502; A61M 2205/52; G16H 20/17; G16H 40/40; G16H 40/63; G16H 40/67

See application file for complete search history.

(56) References Cited

U.S. PATENT DOCUMENTS

| | | | | |
|---|---|---|---|---|
| 5,647,853 | A | 7/1997 | Feldmann et al. | |
| 5,681,285 | A | 10/1997 | Ford et al. | |
| 5,685,844 | A | 11/1997 | Marttila | |
| 5,800,387 | A | 9/1998 | Duffy et al. | |
| 6,248,093 | B1 | 6/2001 | Moberg | |
| 6,269,340 | B1 | 7/2001 | Ford et al. | |
| 6,485,465 | B2 | 11/2002 | Moberg et al. | |
| 8,182,461 | B2 | 5/2012 | Pope et al. | |
| 8,209,060 | B2 | 6/2012 | Ledford | |
| 8,894,631 | B2 | 11/2014 | Mctaggart et al. | |
| 2002/0038392 | A1 | 3/2002 | De La Huerga | |
| 2002/0169636 | A1 | 11/2002 | Eggers et al. | |
| 2007/0219495 | A1 | 9/2007 | Kato et al. | |
| 2011/0238032 | A1 * | 9/2011 | McTaggart | G16H 20/17 700/282 |
| 2012/0157920 | A1 | 6/2012 | Flachbart et al. | |
| 2012/0323170 | A1 | 12/2012 | Lee et al. | |
| 2012/0323212 | A1 | 12/2012 | Murphy | |
| 2015/0041419 | A1 | 2/2015 | Hasegawa | |
| 2016/0074582 | A1 * | 3/2016 | Becker | A61M 5/1723 604/503 |
| 2016/0350513 | A1 * | 12/2016 | Jacobson | G16H 70/40 |

FOREIGN PATENT DOCUMENTS

| | | | |
|---|---|---|---|
| EP | 0354852 | A2 | 2/1990 |
| EP | 0649316 | A1 | 4/1995 |
| EP | 0801578 | A1 | 10/1997 |
| EP | 2869474 | A1 | 5/2015 |
| GB | 2224444 | A | 5/1990 |
| WO | 1994008647 | A1 | 4/1994 |
| WO | 2002011049 | A2 | 2/2002 |
| WO | 2007127880 | A2 | 11/2007 |
| WO | 2008059495 | A2 | 5/2008 |
| WO | 2013052318 | | 4/2013 |
| WO | 2016179389 | A1 | 11/2016 |

OTHER PUBLICATIONS

Search Reported dated Apr. 4, 2019 for EP Application No. 16804015.2; 15 pages.

Office Action dated Dec. 30, 2019 for Chinese Application No. 201680032174.3, 7 pages.

International Search Report for corresponding International Application No. PCT/US2016/034007 dated Sep. 8, 2016; 4 pages.

Written Opinion of the International Searching Authority for corresponding International Application No. PCT/US2016/034007 dated Sep. 8, 2016; 8 pages.

Communication dated Apr. 22, 2021 for EP Application No. 16804015.2, 8 pages.

Search Report dated Jan. 3, 2019 for EP Application No. 16804015.2, 18 pages.

Partial European Search Report dated Nov. 7, 2024 for EP Application No. 24193567.5, 16 pages.

* cited by examiner

PROCEDURE-BASED PROGRAMMING FOR INFUSION PUMPS

CROSS-REFERENCE TO RELATED APPLICATIONS

This application is a continuation of U.S. application Ser. No. 18/150,064, filed Jan. 4, 2023, which is a division of U.S. application Ser. No. 15/578,101, filed Nov. 29, 2017, now U.S. Pat. No. 11,571,513, which is a National Stage Application of PCT/US2016/034007, filed May 25, 2016, which claims the benefit of U.S. Provisional Application No. 62/170,891, filed Jun. 4, 2015, which are hereby fully incorporated herein by reference.

TECHNICAL FIELD

Subject matter hereof relates generally to medical devices, and more particularly, to devices, systems, and methods for procedure-based programming for infusion pumps.

BACKGROUND

Infusion pumps are useful medical devices for managing the delivery and dispensation of infusates such as therapeutic medications and drugs. Infusion pumps provide significant advantages over manual administration of infusates by accurately delivering the infusates over an extended period of time. Infusion pumps are particularly useful for treating diseases and disorders that require regular pharmacological intervention, including cancer, diabetes, and vascular, neurological, and metabolic disorders. Infusion pumps also enhance the ability of healthcare providers to deliver anesthesia and manage pain. Infusion pumps are used in various settings, including hospitals, nursing homes, and other short-term and long-term medical facilities, as well as in residential care settings. There are many types of infusion pumps, including ambulatory, large volume, patient-controlled analgesia (PCA), elastomeric, syringe, enteral, and insulin pumps. Infusion pumps can be used to administer medication through various delivery methods, including intravenously, intraperitoneally, intra-arterially, intradermally, subcutaneously, in close proximity to nerves, and into an intraoperative site, epidural space or subarachnoid space.

For example, syringe pumps and related components are disclosed in U.S. Pat. No. 4,978,335 titled "Infusion Pump with Bar Code Input to Computer," U.S. Pat. No. 8,182,461 titled "Syringe Pump Rapid Occlusion Detection System," and U.S. Pat. No. 8,209,060 titled "Updating Syringe Profiles for a Syringe Pump." Each of these patents is hereby incorporated by reference in its entirety.

Typically, infusion pumps are individually programmed without context to any role or position within a larger medical procedure or patient treatment activity. For example, current drug libraries typically focus on programming one medicament or drug on one pump as directed by a medical practitioner. Concentration limits, volume limits, and other limits or boundaries, as well as other medicament or drug programming parameters are usually set individually for each such infusate and the pump is programmed within those boundaries.

For example, an anesthesiologist in an operating room often operates multiple infusion pumps at the same time. It is not uncommon for several infusion pumps to be employed to deliver various infusates to a single patient. Further, it is not uncommon for multiple surgeries to be performed on multiple patients on the same day. Thus, in a single day, an anesthesiologist in an operating room might operate several sets of infusion pumps with the same or similar medicaments or drugs set to similar or nearly the same respective doses for those multiple surgeries. In traditional infusion systems, the anesthesiologist must spend time programming each of the infusion pumps separately, and respectively program each of the infusion pumps for each surgery. It might take, for example, 30 minutes for the anesthesiologist to program all of the infusion pumps for a single surgery. Over the course of the day, the anesthesiologist could therefore spend several hours programming infusion pumps for the same medicaments or drugs at similar or nearly the same respective doses. This sort of repetitive, individual programming of pumps is laborious, time-consuming, and potentially error-prone.

Therefore there is a need for devices, systems, and methods for procedure-based programming for infusion pumps that can minimize the repetitive, laborious, time-consuming, and potentially error-prone interactions of traditional infusion pump programming tasks.

SUMMARY

Embodiments described or otherwise contemplated herein substantially meet the aforementioned needs. According to an embodiment, a suitably configured drug library allows a medical practitioner to program one or a plurality of pumps according to an activity or procedure by hiding the details of the programming from the practitioner or user. As a result, complex and/or tedious programming of infusion pumps can instead be done easily and efficiently.

According to an embodiment, a hierarchical level comprises an amount of complexity by which a system is viewed or programmed. The higher the level, the less detail is presented to the user. The lower the level, the more detail is presented to the user. In embodiments, a drug library can be grouped according to various hierarchical levels.

In an embodiment, a functional set can comprise a common procedure or common activity in a hospital. For example, a functional set can comprise a particular hospital procedure, such as "cardiac surgery." In another example, a functional set can comprise a set of common infusions that can be administered during other infusions. In still another example, a functional set can comprise practitioner workflow "favorites," or commonly used procedures or activities. In such embodiments, a functional set favorite can be configured to program one or more of a plurality of infusion pumps.

Embodiments described herein can be implemented on, for example, large-volume pumps (LVPs). LVPs can pump large amounts of solution. In embodiments, large-volume pumps can utilize a form of peristaltic pump. LVPs can utilize computer-controlled rollers compressing a tubing through which the medicament flows. In another embodiment, LVPs can utilize a set of fingers that press on the tubing in sequence.

In an embodiment, a system for configuring a plurality of medical devices according to a particular treatment protocol comprises a rack, configured to physically and removably couple the plurality of medical devices thereto; and a router, configured to enable digital communications between the plurality of medical devices that are physically and removably coupled to the rack into a local area network, wherein, when the plurality of medical devices are physically coupled to the rack and communicatively coupled to the local area network through the router, (i) the particular treatment protocol is transmitted to each of the plurality of medical devices and (ii) the plurality of medical devices are able to each responsively provide pre-selected therapies, respectively, corresponding to the particular treatment protocol.

In an embodiment, a method of configuring a plurality of infusion pumps according to a functional set comprises implementing a plurality of infusion pumps, each of the infusion pumps configured to administer infusate to a patient; implementing a drug library, the drug library including at least one functional set defining a set of infusates; receiving input data related to one of the at least one functional sets; obtaining a particular set of infusates from the drug library corresponding to the input data; programming the plurality of infusion pumps according to the set of infusates; and infusing the patient by using the plurality of infusion pumps.

In an embodiment, a system for programming a plurality of infusion pumps comprises a plurality of infusion pumps, each of the infusion pumps configured to administer infusate to a patient; an input source configured to receive a selected functional set; a programming engine including: a drug library including at least one functional set corresponding to the selected functional set defining a set of infusates; a communications engine configured to interface to the plurality of infusion pumps and the input source; a processor configured to interface to the drug library and to command the communications engine to program the plurality of infusion pumps according to the selected functional set.

In an example, one or more of a plurality of infusion pumps can be programmed and coordinated with a real-time embedded server, such as embodiments of the embedded server described in U.S. Patent Application No. 62/158,213, filed on May 7, 2015, which is incorporated herein by reference thereto.

In a feature and advantage of embodiments, a drug library programming of one or more infusion pumps according to a functional set is less error-prone and requires less operator time than traditional programming. In an embodiment, multiple pumps can be automatically programmed by one input step from a user. Or, in embodiments, a number of input steps can be significantly reduced from the number of steps typically required for known infusion pumps. In an embodiment, a selection of a functional set or grouping automatically programs one or a plurality of infusion pumps. For example, an embodiment of programming according to a functional set only requires an operator to select a functional set. Subsequently, a programming command is automatically executed for all required infusion pumps. The operator is then only required to verify, as a fail-safe or safety precaution, that the dose on each pump is correct. Programming is therefore automated according to the selected functional set. In embodiments, an operator can be further required to load appropriate syringes into respective pumps. Such loading acts as a second check on the programming of the pump. Thus, manual input errors are avoided, and programming is streamlined in embodiments.

In another feature and advantage of embodiments, a drug library programming of one or more infusion pumps according to a functional set can speed up infusion delivery. For example, in an emergency situation where many infusions need to be started quickly, a single functional command can be utilized to program multiple infusion pumps. In embodiments, the drug library can be programmed with a plurality of functional commands related to emergency situations or other time-critical infusions.

In another feature and advantage of embodiments, functional sets allow multiple drug deliveries to be grouped together according to a hospital procedure. In embodiments, a plurality of infusion pumps operably coupled to a single patient can be programmed for the hospital procedure the patient is undergoing or about to undergo. For example, in the aforementioned "cardiac surgery," hospital procedure the set of common infusions preparing the patient for the procedure can be programmed into the necessary infusion pumps. For example, a set of infusion pumps can be programmed with the medications sodium bicarbonate, saline, fenoldopam, insoline, remifentanil, and saline such that each of those infusates is delivered to the patient from a separate infusion pump. In other embodiments, a set of infusion pumps can be programmed with the aforementioned infusates such that combinations are infused on a single infusion pump or overlap infusion pumps.

The above summary is not necessarily intended to describe each illustrated embodiment or every implementation of the subject matter hereof. The figures and the detailed description that follow more particularly exemplify these embodiments.

BRIEF DESCRIPTION OF THE DRAWINGS

Subject matter hereof may be more completely understood in consideration of the following detailed description of various embodiments of the subject matter in connection with the accompanying drawings, in which.

Figure 1A:
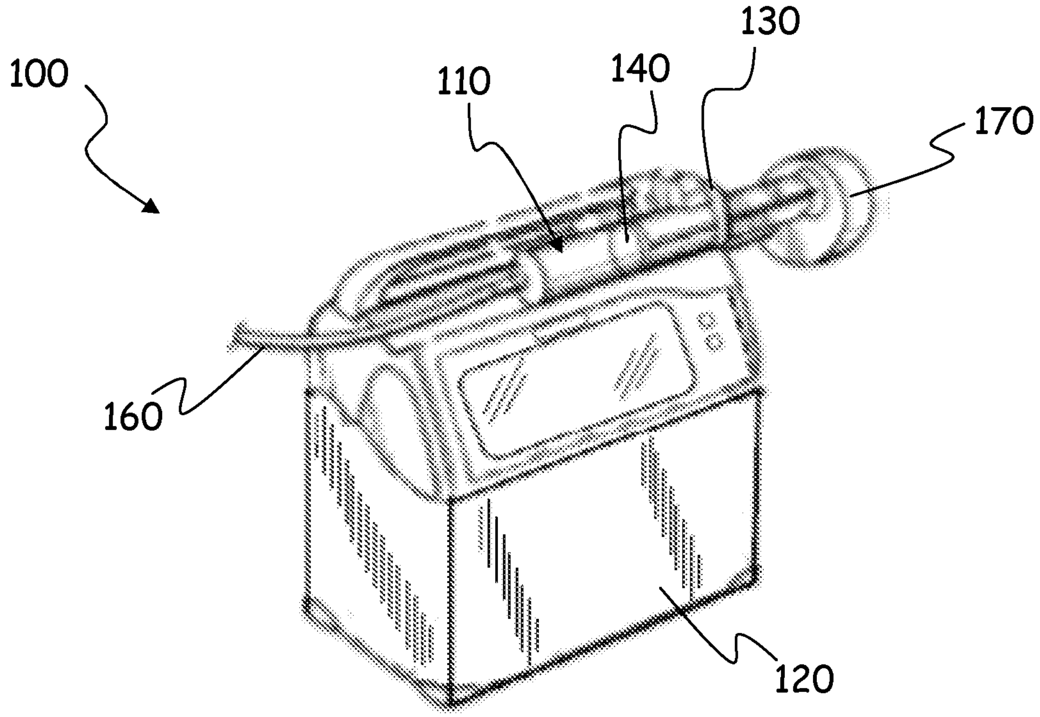
FIG. 1A is a perspective view of a syringe type infusion pump, according to an embodiment.

While embodiments are amenable to various modifications and alternative forms, specifics thereof have been shown by way of example in the drawings and will be described in detail. It should be understood, however, that the intention is not to limit subject matter hereof to the particular embodiments described. On the contrary, the intention is to cover all modifications, equivalents, and alternatives falling within the spirit and scope of subject matter hereof in accordance with the appended claims.

DETAILED DESCRIPTION OF THE DRAWINGS

Figure 1B:
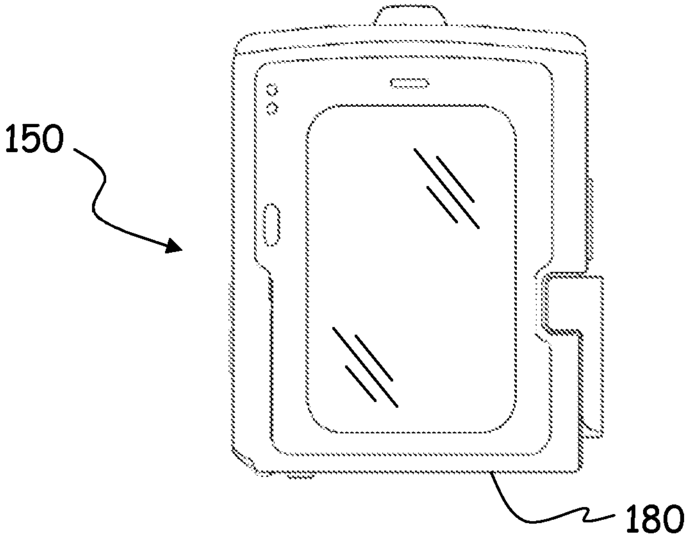
FIG. 1B is a front view of a control module of an ambulatory type infusion pump, according to an embodiment.

FIGS. 1A and 1B show examples of infusion pumps 100 and 150, respectively (also referred to more generally in this disclosure by numeral 100), which can be used to implement embodiments of the systems and methods discussed herein. In general, infusion pump 100 is a syringe-type pump that can be used to deliver a wide range of infusates, drug therapies and treatments. Infusion pump 100 includes a pharmaceutical container or syringe 110, which is supported on and secured to housing 120 by clamp 130, respectively. In embodiments, syringe 110 can be separately supplied from pump 100. In other embodiments, syringe 110 is an integrated component of pump 100. Syringe 110 includes a plunger 140 that forces fluid outwardly from syringe 110 via infusion line 160 that is connected to a patient. A motor and lead screw arrangement internal to housing 120 of pump 100 cooperatively actuates a pusher or plunger driver mechanism 170, to move plunger 140 of syringe 110. In embodiments, a sensor (not shown; which is typically internal to plunger driver mechanism 170) monitors force and/or plunger position in the syringe according to system specifications.

Infusion pump 150 shown in FIG. 1B is an example of an ambulatory-type infusion pump that can be used to deliver a wide range of infusates, drug therapies, and treatments. Such ambulatory pumps can be comfortably worn by or otherwise removably coupled to a user for in-home ambulatory care by way of belts, straps, clips or other simple fastening means, and can also be alternatively provided in ambulatory pole-mounted arrangements within hospitals and other medical care facilities. Infusion pump 150 generally includes a peristaltic type infusion pump mechanism that controls the flow of medication from a reservoir (not shown in FIG. 1B) of fluid coupled to pump 150 through a conduit from the reservoir which can matingly pass along bottom surface 180 of pump 150. The reservoir can comprise a cassette that is attached to the bottom of pump 150 at surface 180, or an IV bag or other fluid source that is similarly connected to pump 150 via an adapter plate (not shown) at surface 180. Specifically, pump 150 uses valves and an expulsor located on bottom surface 180 to selectively squeeze a tube of fluid (not shown) connected to the reservoir to effect the movement of the fluid supplied by the reservoir through the tube and to a patient in peristaltic pumping fashion. Infusion pumps 100 and 150 are two examples of infusion pumps that can be suitable for use with embodiments discussed herein, though other pumps and devices can be used in other embodiments of infusion systems utilizing subject matter hereof.

Figure 2:
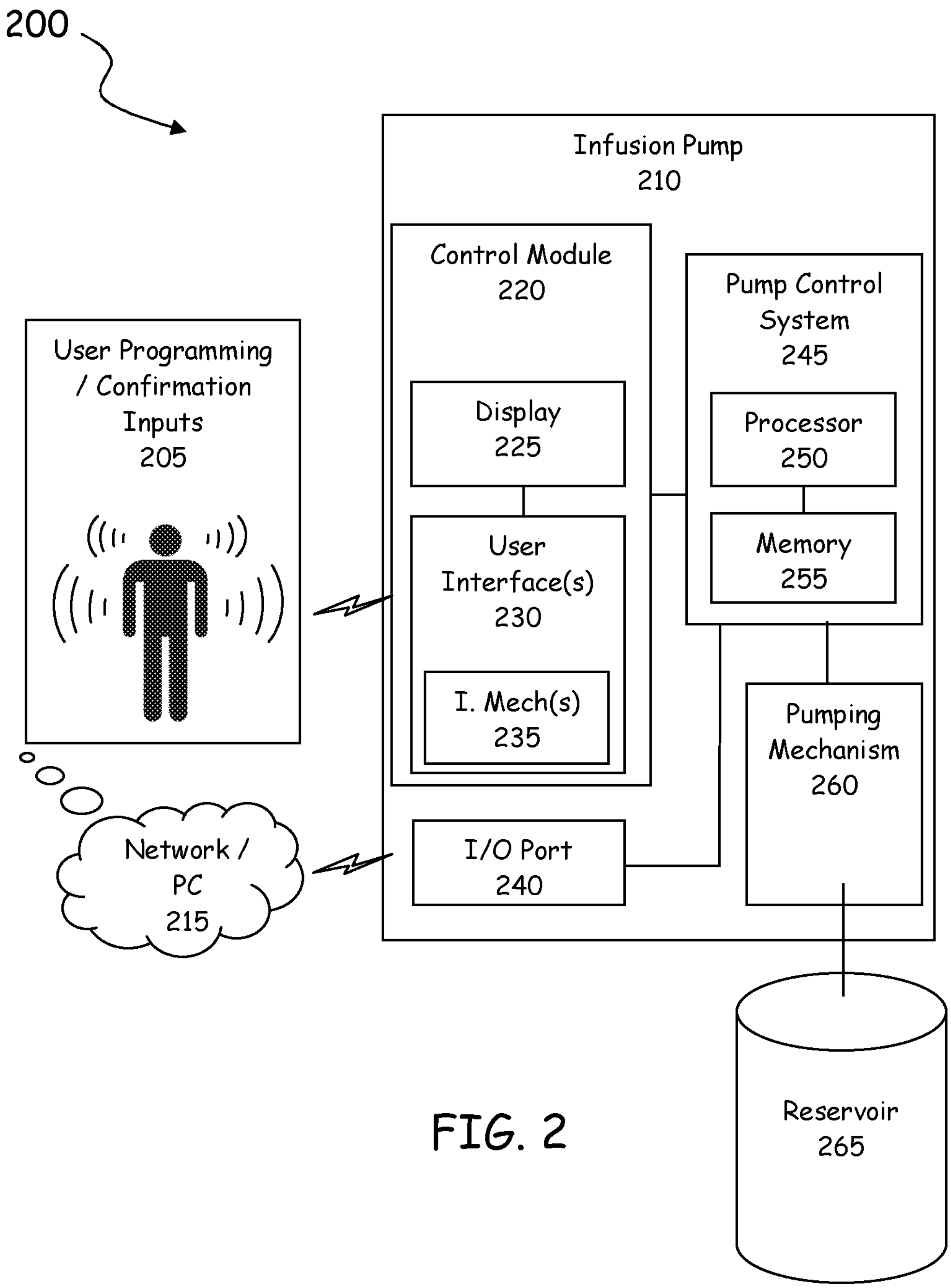
FIG. 2 is a block diagram of an infusion pump system, according to an embodiment.

FIG. 2 is a schematic diagram of an infusion pump system 200. System 200 includes infusion pump 210 having pump control system 245 with processor 250 and memory 255 programmable with selected protocols, profiles, segments of profiles, and other settings for controlling operation of pumping mechanism 260 such as, for example, the aforementioned syringe and ambulatory or peristaltic type mechanisms. In an embodiment, memory 255 can comprise a drug library or portions thereof configured for programming according to the functional sets described herein.

In an embodiment, processor 250 can be any programmable device that accepts digital data as input, is configured to process the input according to instructions or algorithms, and provides results as outputs. In an embodiment, processor 250 can be a central processing unit (CPU) configured to carry out the instructions of a computer program. In another embodiment, processor 250 can be an application specific integrated circuit (ASIC). In another embodiment, processor 250 can be a field-programmable gate array (FPGA). Processor 250 is therefore configured to perform arithmetical, logical, and input/output operations.

Memory 255 can comprise volatile or non-volatile memory as required by the coupled processor 255 to not only provide space to execute the instructions or algorithms, but to provide the space to store the instructions themselves. In embodiments, volatile memory can include random access memory (RAM), dynamic random access memory (DRAM), or static random access memory (SRAM), for example. In embodiments, non-volatile memory can include read-only memory, flash memory, ferroelectric RAM, hard disk, floppy disk, magnetic tape, or optical disc storage, for example. The foregoing lists in no way limit the type of memory that can be used, as these embodiments are given only by way of example and are not intended to limit the scope of subject matter hereof.

Infusion pump 200 can also include control module 220 (e.g., a user interface) for relaying commands to pump control system 245. Control module 220 includes at least one user interface 230 utilizing operator input technology including input mechanism(s) 235, which work with display 225. In some cases display 225 will be considered part of user interface(s) 230. User interface 230 generally allows a user to enter various parameters, including but not limited to names, drug information, limits, delivery shapes, information relating to hospital facilities, as well as various user-specific parameters (e.g., patient age and/or weight). Infusion pump 210 can include a USB port, Ethernet, Wi-Fi or other appropriate input/output (I/O) interface port 240 for connecting infusion pump 210 to network or computer 215 having software designed to interface with infusion pump 210. In an embodiment, network or computer 215 can transmit a drug library or portions thereof for programming according to the functional sets described herein. For example, network or computer 215 can comprise an embedded server system for controlling, in real-time, infusion pump 200. In embodiments, control module 220 can be automatically configured according to data from network or computer 215 (or the embedded server) for programming according to functional sets.

Power to infusion pump 210 is accomplished via an AC or DC power cord or any suitable battery source. Embodiments can also include a wireless power source. User inputs 205 to the system can be provided by programming from a user, such as a patient, pharmacist, scientist, drug program designer, medical engineer, nurse, physician, or other medical practitioner or healthcare provider. User inputs 205 may utilize direct interfacing (i.e., a keyboard or other touch-based inputs) or user inputs 205 may utilize indirect or "touchless" interfacing (i.e., gestures; voice commands; facial movements or expressions; finger, hand, head, body and arm movements; or other inputs that do not require physical contact). User inputs 205 are generally interfaced, communicated, sensed, and/or received by operator input mechanisms 235 of user interface 230. Operator input mechanisms 235 may include, for example, keyboards, touch screens, cameras, or sensors of electric field, capacitance, or sound.

As depicted in FIG. 2, infusion pump 210 is operably coupled to reservoir 265 via pumping mechanism 260. In embodiments, reservoir 265 can comprise any suitable infusate supply, such as an IV bag, syringe, continuous supply, or other infusate storage. In an embodiment, reservoir 265 is coupled to pumping mechanism 260 by cannula suitable for transferring infusate stored in reservoir 265 to pumping mechanism 260.

Figure 3:
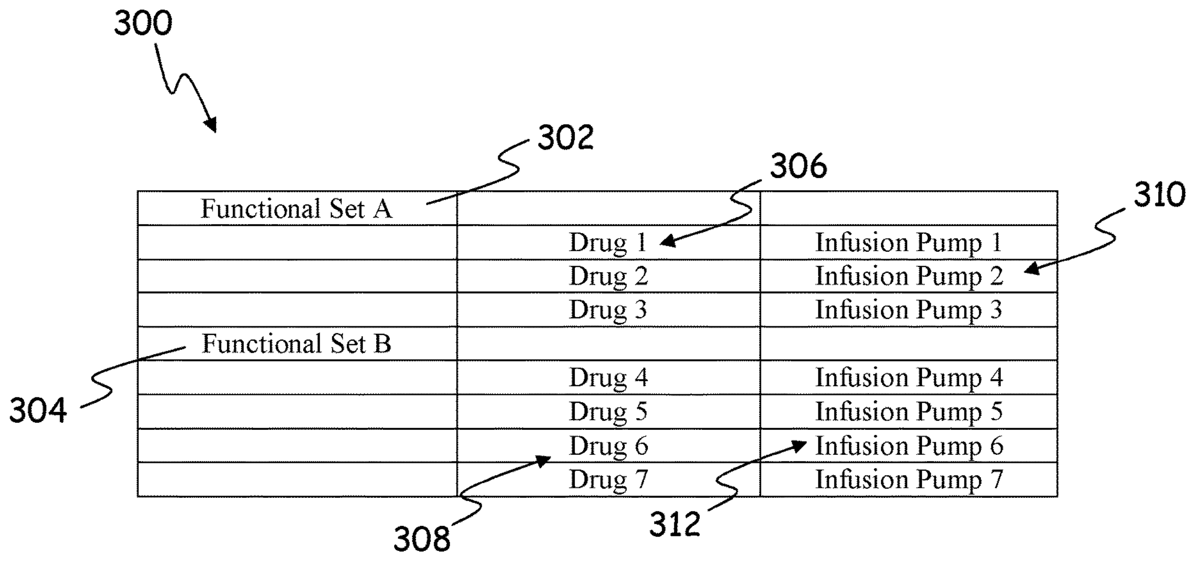
FIG. 3 is a block diagram of a portion of a generic drug library including functional sets, according to an embodiment.

Referring to FIG. 3, a block diagram of a portion of a generic drug library 300 including functional sets is depicted, according to an embodiment. Drug library 300 generally comprises Functional Set A 302 and Functional Set B 304. For example, Functional Set A 302 can comprise a department-level procedure for emergencies, in an emergency room department. In another example Functional Set B 304 can comprise a particular procedure for a particular department, such as cardiac surgery.

Functional Set A 302 comprises a set of medications 306 to be infused. For example, set of medications 306 can be defined by Drug 1, Drug 2, and Drug 3, as depicted in FIG. 3. Each of the individual medications in set of medications 306 can be utilized to individually address a need of Functional Set A 302. In an embodiment, in combination, the individual medications within set of medications 306 are configured to complement each other to positively affect the patient being infused. In other embodiments, a medical practitioner can select among set of medications 306 for infusion. For example, only Drug 1 and Drug 3 might be utilized for a particular patient. Drug library 300 allows for easy selection of subgroups of set of medications 306. Likewise, Functional Set B 304 comprises a set of medications 308 to be infused. For example, set of medications 308 can be defined by Drug 4, Drug 5, Drug 6, and Drug 7, as depicted in FIG. 3.

Set of medications 306, and particularly, Drug 1, Drug 2, and Drug 3 can be respectively configured for programming on a particular set of pumps 310. For example, set of pumps 310 can generally include Infusion Pump 1, Infusion Pump 2, and Infusion Pump 3. In an embodiment, Drug 1 can be configured for programming on Infusion Pump 1, Drug 2 can be configured for programming on Infusion Pump 2, and Drug 3 can be configured for programming on Infusion Pump 3. In other embodiments (not shown), set of infusions 306 can be defined such that pumps can be programmed ad-hoc. Likewise, set of infusions 308, and particularly, Drug 4, Drug 5, Drug 6, and Drug 7 can be respectively configured for programming on a particular set of pumps 312. For example, set of pumps 312 can generally include Infusion Pump 4, Infusion Pump 5, Infusion Pump 6, and Infusion Pump 7.

Therefore, by selecting Functional Set A 302, a medical practitioner can program the infusions defined by set of medications 306 on set of pumps 310. Likewise, by selecting Functional Set B 304, a medical practitioner can program the infusions defined by set of medications 308 on set of pumps 312.

Figure 4:
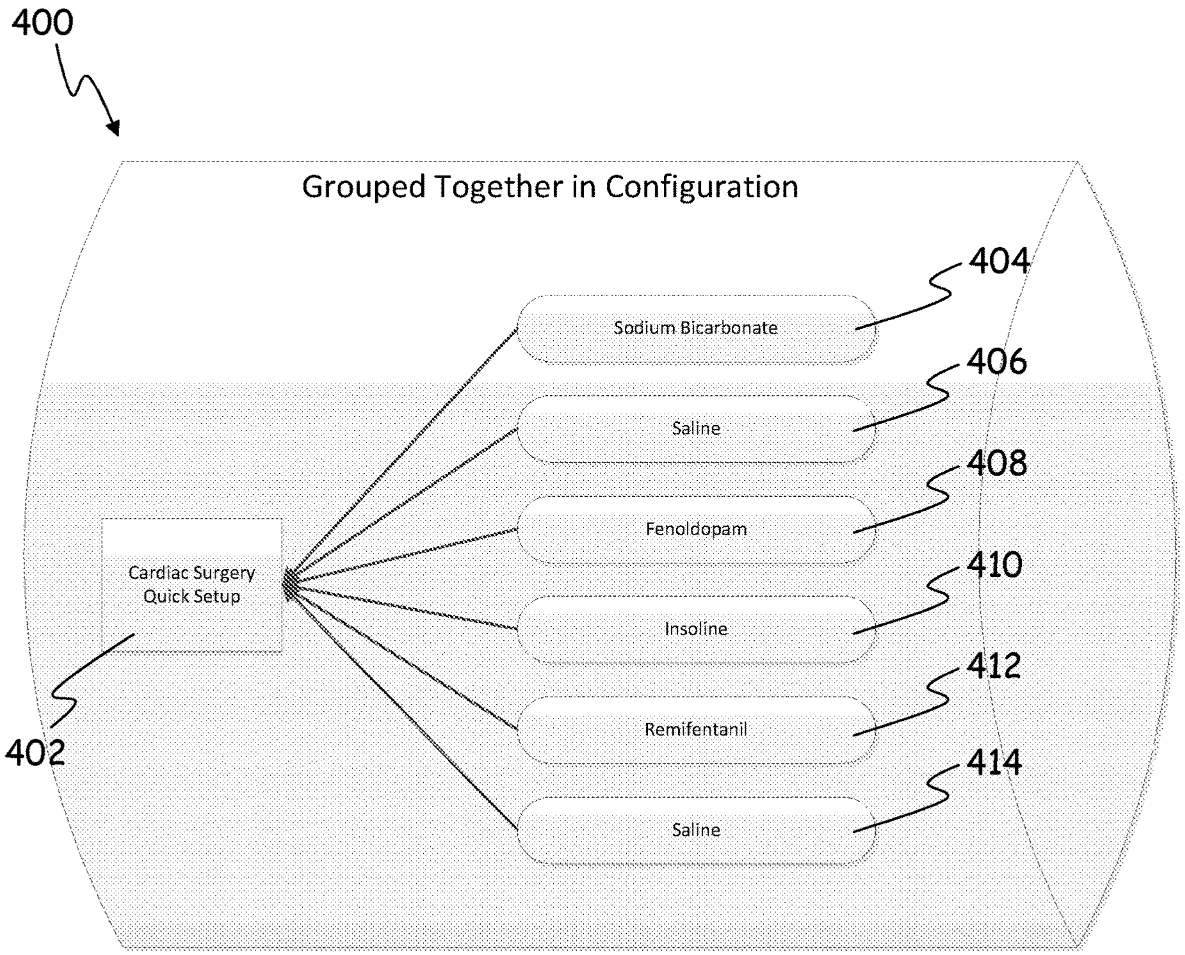
FIG. 4 is a block diagram of a procedure-based programming configuration of a cardiac surgery procedure, according to an embodiment.

Referring to FIG. 4, a block diagram of a procedure-based programming configuration 400 for a cardiac surgery procedure 402 is depicted, according to an embodiment. Configuration 400 generally comprises a quick setup procedure, such as cardiac surgery procedure 402.

Cardiac surgery procedure 402 comprises a set of infusates 404-414. For example, cardiac surgery procedure 402 can comprise a programming configuration for an infusion pump for sodium bicarbonate 404, a programming configuration for an infusion pump for saline 406, a programming configuration for an infusion pump for fenoldopam 408, a programming configuration for an infusion pump for insoline 410, a programming configuration for an infusion pump for remifentanil 412, and a programming configuration for an infusion pump for saline 414.

In an embodiment, a drug library can be utilized that defines a set of medications for the procedure 402 and the infusates 404-414, such as drug library 300. Optionally, and as described with respect to drug library 300, the drug library can define a set of pumps for administering the set of infusates. As a result, a drug library, such as drug library 300, can comprise a "Workflow Management" programming configuration or "Procedure Management" programming configuration option. Drug library 300 therefore supports more than one pump being programmed concurrently. In another embodiment, a "Workflow Management" programming configuration or "Procedure Management" programming configuration option can be selected on a pump, such as infusion pump 210 in FIG. 2.

Figure 5:
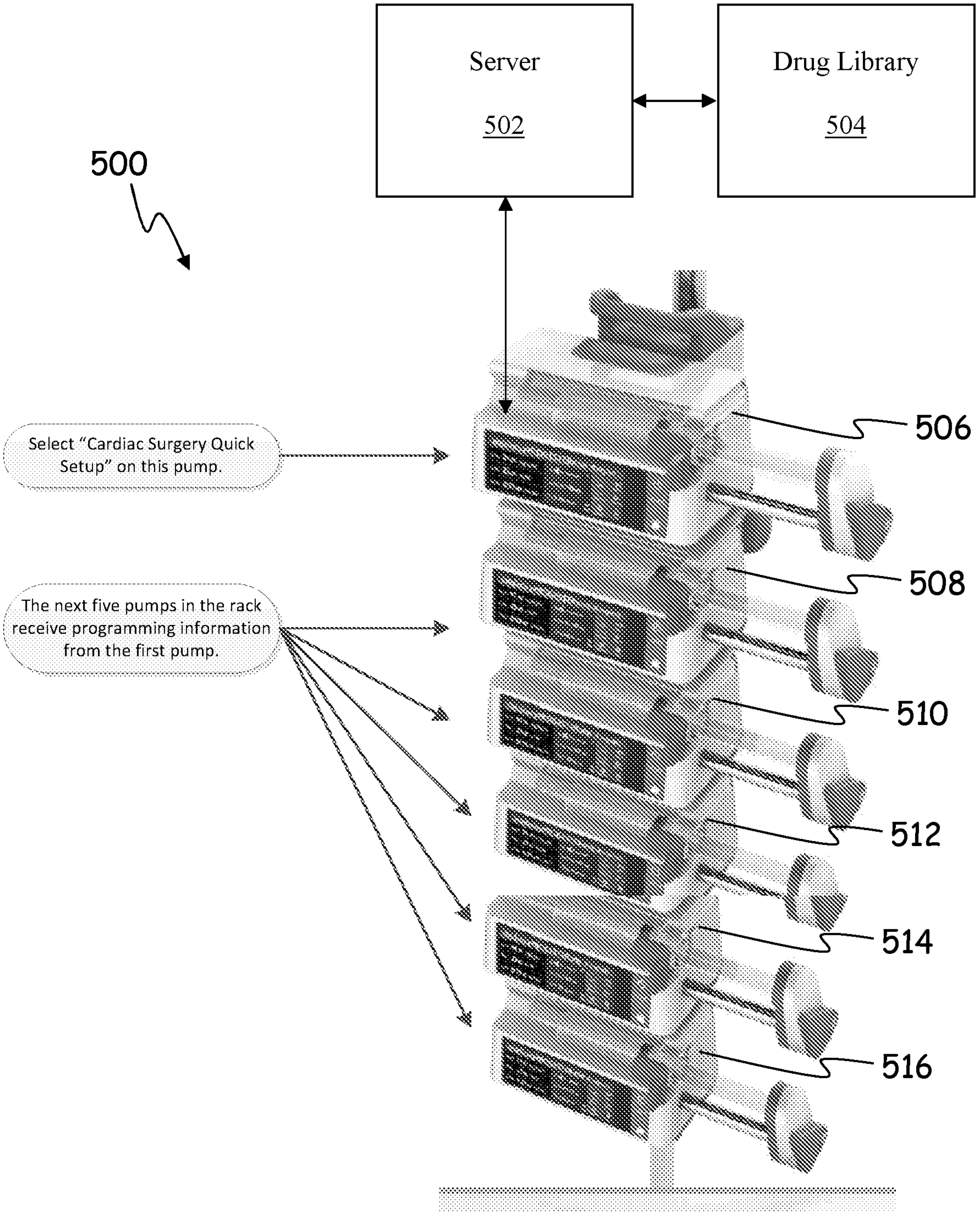
FIG. 5 is an annotated block diagram of a system for programming a set of infusion pumps for the procedure-based programming of the cardiac surgery procedure of FIG. 4, according to an embodiment.

Referring to FIG. 5, an annotated block diagram of a system 500 for programming a set of infusion pumps for functional set programming is depicted, according to an embodiment. In particular, system 500 is configured for the programming of the cardiac surgery procedure of FIG. 4 System 500 generally comprises a server 502, a drug library 504, and a set of infusion pumps 506-516.

In embodiments, set of infusion pumps 506-516 can be operably coupled to a networked rack. The rack can be configured to physically and removably couple the set of infusion pumps 506-516. In an embodiment, the rack further comprises a router configured to enable digital communications between the set of infusion pumps 506-516. For example, a router and set of infusion pumps 506-516 can comprise a local area network such the set of infusion pumps 506-516 are physically coupled to the rack and electrically coupled to the local area network through the router.

In an embodiment, server 502 comprises a processor and a memory. In an embodiment, the processor can be any programmable device that accepts digital data as input, is configured to process the input according to instructions or algorithms, and provides results as outputs. In an embodiment, the processor can be a central processing unit (CPU) configured to carry out the instructions of a computer program. In another embodiment, the processor can be an application specific integrated circuit (ASIC). In another embodiment, the processor can be a field-programmable gate array (FPGA). The processor is therefore configured to perform basic arithmetical, logical, and input/output operations.

The memory can comprise volatile or non-volatile memory as required by the coupled processor to not only provide space to execute the instructions or algorithms, but to provide the space to store the instructions themselves. In embodiments, volatile memory can include random access memory (RAM), dynamic random access memory (DRAM), or static random access memory (SRAM), for example. In embodiments, non-volatile memory can include read-only memory, flash memory, ferroelectric RAM, hard disk, floppy disk, magnetic tape, or optical disc storage, for example. In an embodiment, the memory can comprise a database. In an embodiment, the memory comprises memory for operation of the processor and a separate database for storing records related to the system. The foregoing lists in no way limit the type of memory that can be used, as these embodiments are given only by way of example and are not intended to limit the scope of the subject matter hereof.

A plurality of engines can be implemented by or according to the processor and memory of server 502. For example, any number of engines can be configured to coordinate the programming of the set of pumps 506-516, as directed by drug library 504. As such, server 502 is communicatively coupled to at least one of infusion pumps 506-516. In an embodiment, referring to infusion pump system 200 in FIG. 2, server 502 comprises a network or computer similar to network or computer 215 having software designed to interface with infusion pumps 506-516. In an embodiment, server 502 can comprise a real-time embedded server, such as embodiments of the embedded server described in the aforementioned U.S. Patent Application No. 62/158,213. It is therefore to be appreciated and understood that, although depicted in FIG. 5 separately from pumps 506-516, server 502 could physically reside in the rack or even in one of pumps 506-516.

Server 502 can be configured to transmit a set of programming instructions that comprise part of a functional set larger than programming for a single pump. For example, a set of programming instructions can comprise a unique programming configuration for each coupled pump. In an embodiment, the set of programming instructions comprises a batch programming command that contains the programming instructions for all coupled pumps 506-516. In such embodiments, each pump is only programmed according to the particular instructions intended for that particular pump but receives the batch or aggregated programming instructions for all pumps. In embodiments, pump identifiers or other unique data sets can be utilized to parse the batch programming command. In another embodiment, server 502 individually transmits the programming instructions for all coupled pumps 506-516 to each of the coupled pumps 506-516. In still another embodiment, one of pumps 506-516 further directs the programming command after receipt from server 502.

Drug library 504 comprises a database of functional sets including a set of medications to be infused for each level such as, for example, the aforementioned department-level procedure for emergencies. In an embodiment, drug library 504 is substantially similar to the portion of drug library 300 depicted in FIG. 3. For example, drug library 504 can comprise cardiac surgery procedure 402 and set of medications 404-414 as depicted and described with respect to FIG. 4. Referring again to FIG. 5, as depicted, drug library 504 is operably coupled to server 502. In an embodiment, drug library 504 can be embodied on server 502. In another embodiment, drug library 504 can be embodied on a separate database accessible by server 502.

Each of set of pumps 506-516 can be substantially similar to infusion pump 210 as depicted and described with respect to FIG. 2. In an embodiment, set of pumps 506-516 are communicatively coupled to each other. For example, pump 506 can be operably and communicatively coupled to each of pumps 508-516 such that pump 506 can command programming to each of pumps 508-516. In another example embodiment, each of pumps 506-516 is communicatively coupled to server 502. In embodiments, pumps 506-516 can be communicatively coupled such that data, commands, messages, or any other information specific to one of pumps 506-516 can be passed to any of the other pumps 506-516. For example, pumps 506-516 can be operably coupled to a networked rack.

In operation, as depicted by the annotations in FIG. 5, server 502 communicates with drug library 504 to define the functional set programming for pumps 506-516. Server 502 communicates with pump 506 after a functional set programming is selected on pump 506. In another embodiment, functional set programming is initiated by server 502. In another embodiment, a clinician interfaces with one of associated pumps and selects the desired work flow for the upcoming procedure. This pump then sends programming information to the other of the associated plurality of pumps 506-516. The programming information can include infusion information such as drug, dose, concentration, and weight, as needed per the infusion type. In an embodiment, after the initial programming, the pumps do not automatically control each other.

As depicted in FIG. 5, “Cardiac Surgery Quick Setup” is selected on pump 506. Pump 506 interfaces with server 502, and pump 506 is correspondingly programmed for a particular infusion defined by the functional set infusions for Cardiac Surgery. For example, referring again to FIG. 4, and cardiac surgery procedure 402, pump 506 can be programmed for an infusion of sodium bicarbonate 404. Subsequently or concurrently with the programming of pump 506, pumps 508-516 receive programming information from pump 506. In an embodiment, pump 506 can transmit a programming command to pumps 508-516. For example, in an embodiment, and referring again to FIG. 4, pump 508 is programmed for an infusion of saline 406. Pump 510 is programmed for an infusion of fenoldopam 408. Pump 512 is programmed for an infusion of insoline 410. Pump 514 is programmed for an infusion of remifentanil 412. Pump 516 is programmed for an infusion of saline 414. In another embodiment (not depicted), server 502 transmits a programming instruction separately to each of pumps 506-516 in either a batched command or individual commands unique to each pump. Irrespective of a particular programming architecture, pumps 506-516 to be used in the procedure are thus associated with each other. Pumps 506-516 could be associated by being plugged into the same rack or they could be associated manually through serial number, MAC (media access control) address, same subnet, barcode, or any other suitable association method.

Figure 6:
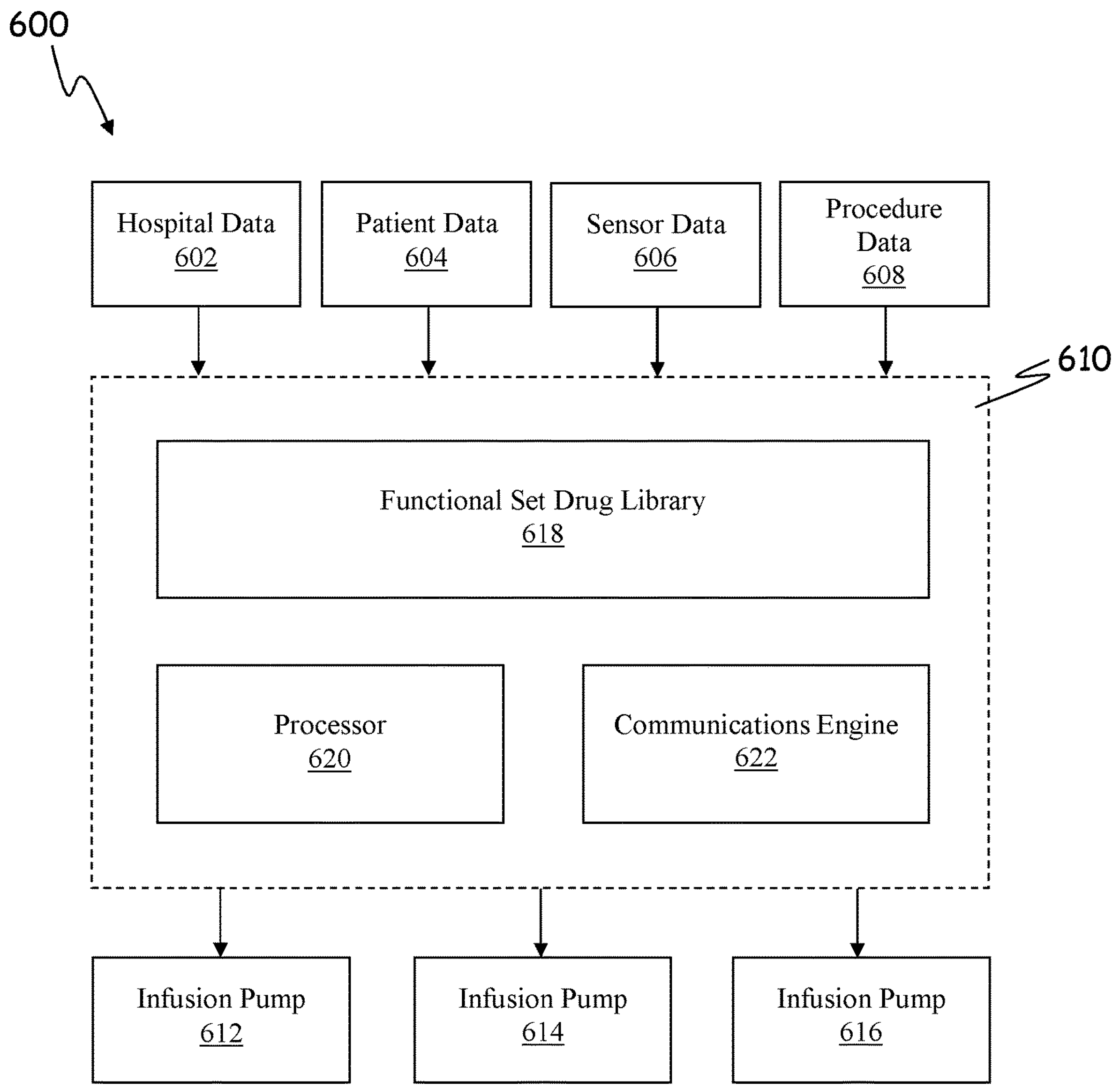
FIG. 6 is a block diagram of a system for procedure-based programming a set of infusion pumps for according to a functional set, according to an embodiment.

Referring to FIG. 6, a block diagram of a system 600 for programming a set of infusion pumps according to a functional set is depicted, according to an embodiment. System 600 generally comprises inputs of hospital data 602, patient data 604, sensor data 606, and procedure data 608 into programming engine 610 for programming of a plurality of infusion pumps 612-616.

Hospital data 602 generally comprises hospital-level data or information related to infusions. For example, hospital data 602 can comprise hospital procedures, standards, configurations, and other hospital-centric information.

Patient data 604 generally comprises patient-specific data or information. For example, patient data 604 can comprise patient height, patient weight, patient gender, patient ID, allergy information, and any other suitable patient-specific information.

Sensor data 606 generally comprises readings, levels, or other statuses provided by any sensors configured for sensing information about the patient. For example, sensor data 606 can comprise temperature data, pulse rate, breathing rate, blood oxygen levels, and blood pressure, and any other suitable sensor data.

Procedure data 608 generally comprises a functional set selection of a set of medications to be infused. In an embodiment, procedure data 608 can comprise a functional set selection as defined by FIG. 3 and, for example, Functional Set A 302 or Functional Set B 304. For example, procedure data 608 can comprise “Cardiac Surgery Quick Setup” as depicted in FIG. 4.

In embodiments, hospital data 602, patient data 604, sensor data 606, and procedure data 608 can be received by communications engine 622 from a respective sending apparatus. For example, a Hospital Information System (HIS) can transmit hospital data 602 and/or patient data 604 to communications engine 622. Each of the respective sensors configured to sense characteristics about or related to the patient can transmit the respective sensor data 606 to communications engine 622. Procedure data 608 can be selected or input as described with respect to FIG. 5 and subsequently transmitted to communications engine 622. In embodiments, additional or fewer data inputs can be utilized by system 600.

Programming engine 610 generally comprises a functional set drug library 618, a processor 620, and a communications engine 622. In an embodiment, programming engine 610 is embodied on a discrete server, such as server 502 as depicted in FIG. 5. However, in other embodiments, programming engine 610 is embodied on an individual medical device, such as one of the plurality of coupled infusion pumps 612-616. In other embodiments, portions of the engines described herein can be spread across multiple devices, such as a discrete server or an infusion pump.

The engines described herein can be constructed, programmed, configured, or otherwise adapted, to autonomously carry out a function or set of functions. The term engine as used throughout this document is defined as a real-world device, component, or arrangement of components implemented using hardware, such as by an application specific integrated circuit (ASIC) or field-programmable gate array (FPGA), for example, or as a combination of hardware and software, such as by a microprocessor system and a set of program instructions that cause the engine to implement the particular functionality, which (while being executed) transform the microprocessor system into a special-purpose device. An engine can also be implemented as a combination of the two, with certain functions facilitated by hardware alone, and other functions facilitated by a combination of hardware and software. In certain implementations, at least a portion, and in some cases, all, of an engine can be executed on the processor(s) of one or more computing platforms that are made up of hardware (e.g., one or more processors, data storage devices such as memory or drive storage, input/output facilities such as network interface devices, video devices, keyboards, mouse or touchscreen devices, etc.) that execute an operating system, system programs, and application programs, while also implementing the engine using multitasking, multithreading, distributed (e.g., cluster, peer-peer, cloud, etc.) processing where appropriate, or other such techniques. Accordingly, each engine can be realized in a variety of physically embodied configurations, and should generally not be limited to any particular implementation exemplified herein, unless such limitations are expressly called out. In addition, an engine can itself be composed of more than one sub-engines, each of which can be regarded as an engine in its own right. Moreover, in the embodiments described herein, each of the various engines corresponds to a defined autonomous functionality; however, it should be understood that in other contemplated embodiments, each functionality can be distributed to more than one engine. Likewise, in other contemplated embodiments, multiple defined functionalities may be implemented by a single engine that performs those multiple functions, possibly in parallel or series with, and/or complementary to other functions, or distributed differently among a set of engines than specifically illustrated in the examples herein.

Drug library 618 comprises a database of functional sets including a set of medications to be infused for each level. In an embodiment, drug library 618 is substantially similar to the portion of drug library 300 depicted in FIG. 3. In embodiments, drug library 618 can comprise a set of medications defining the respective medication amounts and infusion rates that are varied depending on a number of factors, including inputs related to hospital data 602, patient data 604, and sensor data 606. For example, the amounts and infusion rates of the set of medications for a selected functional set for a 200 lb male patient can be significantly different than for a 130 lb female patient. Drug library 618 is configured to store these differing sets of medications. As such, multiple sets of medications can be defined for each functional set.

Processor 620 comprises processing logic and suitable hardware for implementing the processing logic to evaluate received hospital data 602, patient data 604, sensor data 606, and procedure data 608 and determine an appropriate set of infusions from drug library 618. Processor 620 is further configured to command programming of a set of infusions to infusion pumps 612-616. In embodiments, processor 620 can be operably coupled to memory (not shown in FIG. 6).

In embodiments, processor 620 is further configured to suggest or automatically adjust the previously-determined set of infusions or infusion parameters. For example, additional hospital data 602, patient data 604, sensor data 606, and/or procedure data 608 can be received and evaluated to modify or adjust infusion parameters. In an embodiment, such additional hospital data 602, patient data 604, sensor data 606, and/or procedure data 608 can be received and evaluated after the initial set of infusions or infusion parameters have been commanded and are operational. In embodiments, evaluation of hospital data 602, patient data 604, sensor data 606, and/or procedure data 608 can be on regular intervals or continuous.

Communications engine 622 comprises communication logic and suitable hardware for receiving hospital data 602, patient data 604, sensor data 606, and procedure data 608. Further, communications engine 622 comprises communication logic and suitable hardware for transmitting programming commands to infusion pumps 612-616.

Each of infusion pumps 612-616 can be substantially similar to infusion pump 210 as depicted and described with respect to FIG. 2. In embodiments, additional or fewer infusion pumps can be programmed.

In operation, system 600 is configured for the programming of infusion pumps 612-616 according to a functional set. Hospital data 602, patient data 604, sensor data 606, and procedure data 608 are input into programming engine 610. In an embodiment, hospital data 602, patient data 604, sensor data 606, and procedure data 608 are received by communications engine 622. In an embodiment, the data received by communications engine 622 is stored. For example, memory operably coupled to processor 620 can store the received data.

Processor 620 evaluates received hospital data 602, patient data 604, sensor data 606, and procedure data 608 in view of drug library 618. For example, as selected by procedure data 608, a set of medications to be infused is chosen. Processor 620 can then utilize drug library 618 in view of received hospital data 602, patient data 604, and sensor data 606 to select a particular set of medications specific for the unique combination defined by the received data.

Subsequently, processor 620 transmits a programming signal to any of infusion pump 612, infusion pump 614, infusion pump 616, or additional infusion pumps (not shown in FIG. 6). As a result, the pumps receiving the programming signal, such as infusion pump 612, infusion pump 614, infusion pump 616, or additional infusion pumps, are programmed for the respective infusion defined by drug library 618 for the selected procedure data 608 and the unique combination defined by the received hospital data 602, patient data 604, and sensor data 606.

According to embodiments, grouping principles such as functional sets can be applied such that a hierarchy is adhered to so that higher levels are placed near the "top" with more specific concepts underneath. The higher the level, the less detail is presented to the user. The lower the level, the more detail is presented to the user. In embodiments, a drug library can be grouped according to various functional set hierarchies.

Figure 7A:
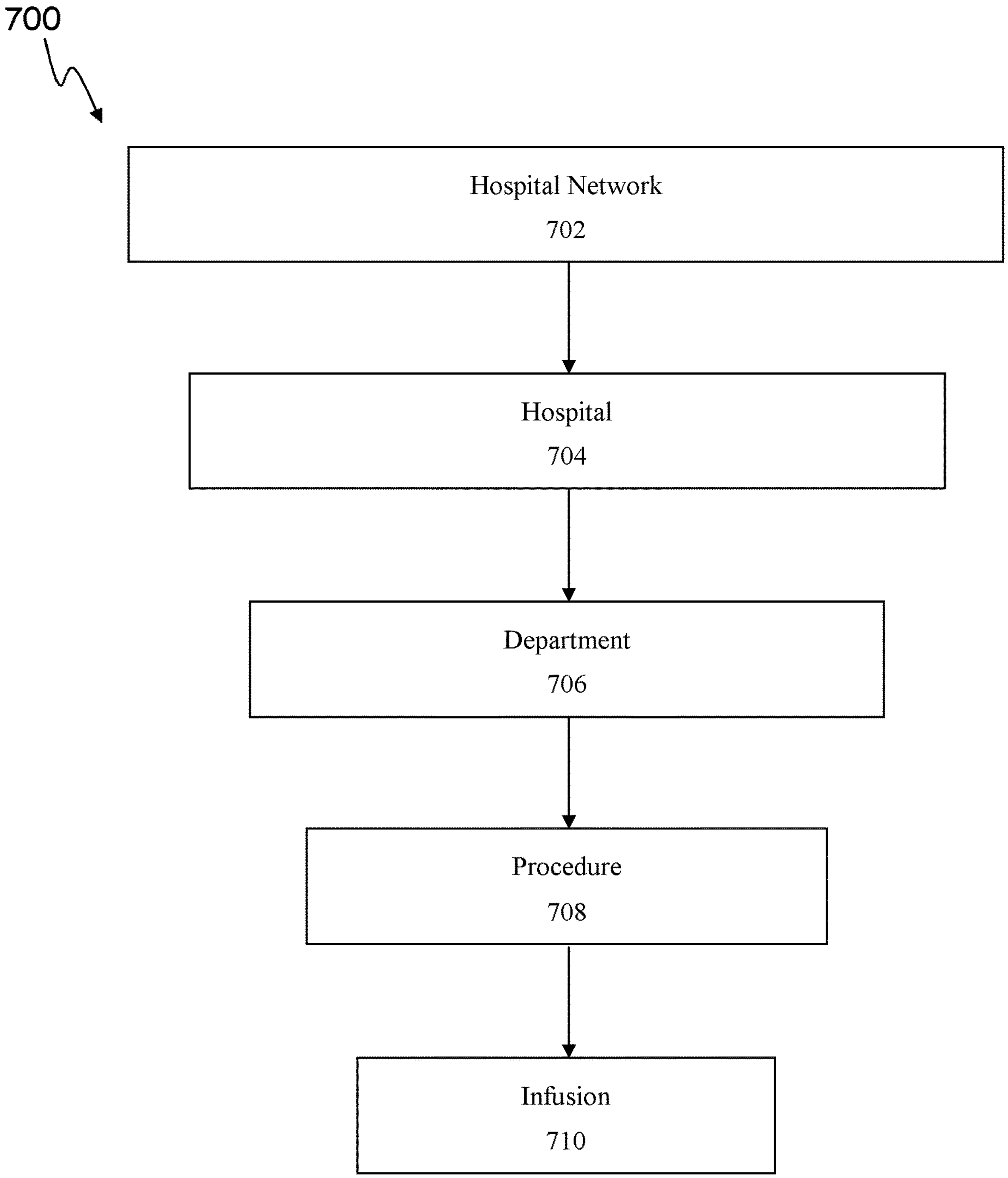
FIG. 7A is a block diagram of an example hierarchy in a hospital network, according to an embodiment.

For example, referring to FIG. 7A, a block diagram of an example functional set according to a hierarchy 700 in a hospital network is depicted, according to an embodiment. Hierarchy 700 generally comprises a hospital network level 702, a hospital level 704, a department level 706, a procedure level 708, and an infusion level 710.

As depicted, hospital network 702 generally comprises one or more hospitals 704. A particular hospital 704 generally comprises one or departments 706. A particular department 706 generally comprises one or more procedures 708. Each procedure 708 generally comprises one or more infusions 710. In embodiments, any of the aforementioned levels can be omitted such that programming of infusions does not adhere to the hierarchical flow depicted in FIG. 7A. For example, depending on the procedures and guidelines for the particular hospital network 702 and/or hospital 704, additional or fewer functional sets can be utilized.

In embodiments, referring again to FIG. 7A, programming hierarchies can be implemented at any of the aforementioned levels. As a result, programming hierarchies can be carried down through the lower functional sets. For example, at hospital network 702, generalized infusions 710 common to all hospitals 704 in hospital network 702 can be defined. In turn, all of the generalized infusions 710 common to all hospitals 704 in hospital network 702 are carried through the lower levels and thus available to all departments 706 and procedures 708. In this way, particular hospital networks 702 can define sets of infusions 710 unique to that hospital network 702.

Likewise, at hospital 704, generalized infusions 710 common to all departments 706 in a particular hospital 704 can be defined. In turn, all of the generalized infusions 710 common to all departments 706 in hospital 704 are carried through the lower levels and thus available to all procedures 708. In this way, particular hospitals 704 can define sets of infusions 710 unique to that hospital 704.

Similarly, each department 706 can define sets of infusions 710 unique to that particular department 706. For example, infusions 710 that are specific to the "surgery" department 706 can be implemented such that the higher level infusion definitions are available for use, as well as the surgery-specific infusions defined at the department 706 level.

Figure 7B:
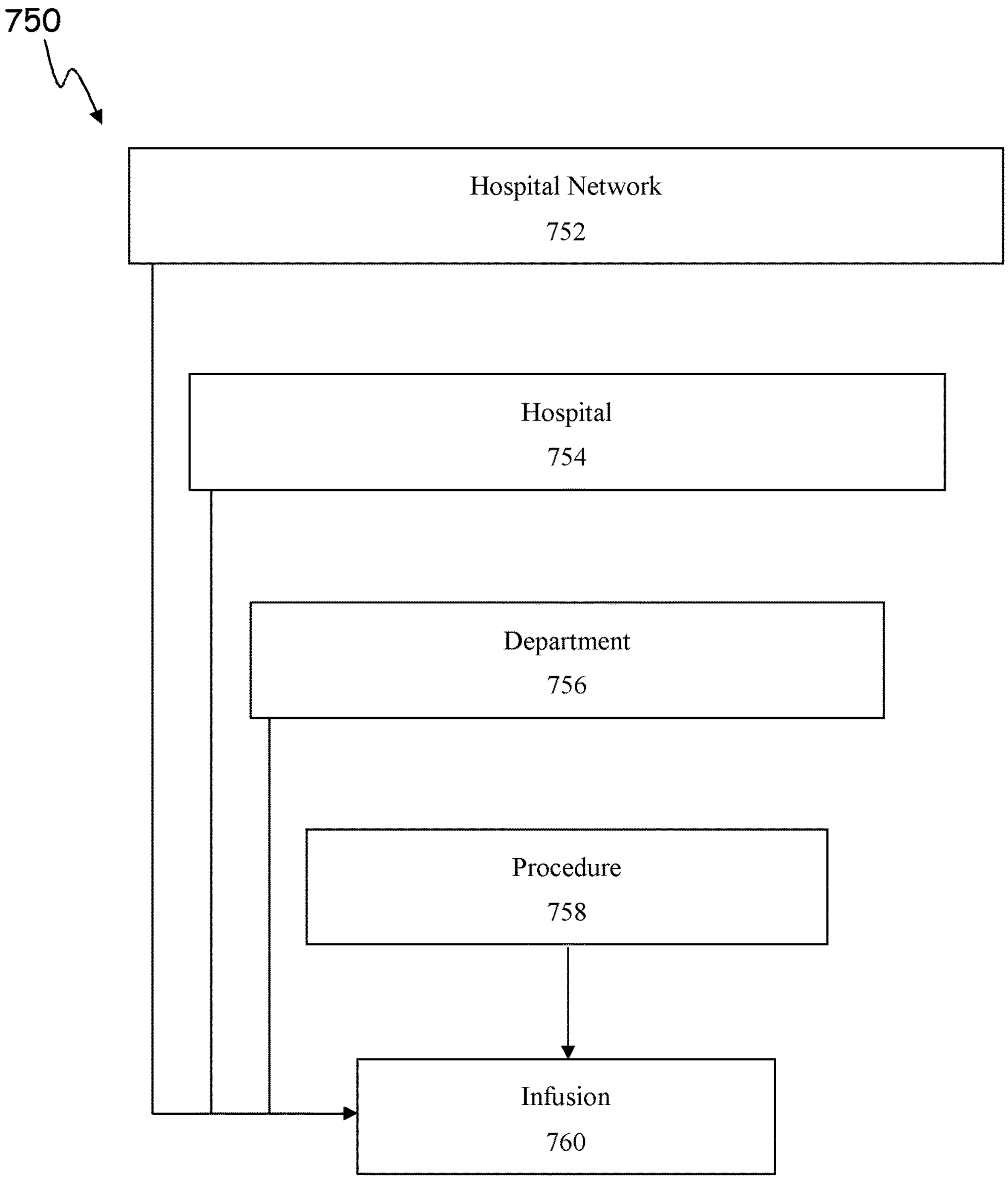
FIG. 7B is a block diagram of an example hierarchy in a hospital network, according to an embodiment.

In another example, referring to FIG. 7B, a block diagram of an example hierarchy 750 in a hospital network is depicted, according to an embodiment. Hierarchy 750 generally comprises a hospital network level 752, a hospital level 754, a department level 756, a procedure level 758, and an infusion level 760. In the example depicted, infusions 760 can be defined at any level within hierarchy 750. In embodiments, infusions 760 are defined such that no generalized infusions are carried through the lower functional sets.

Figure 8:
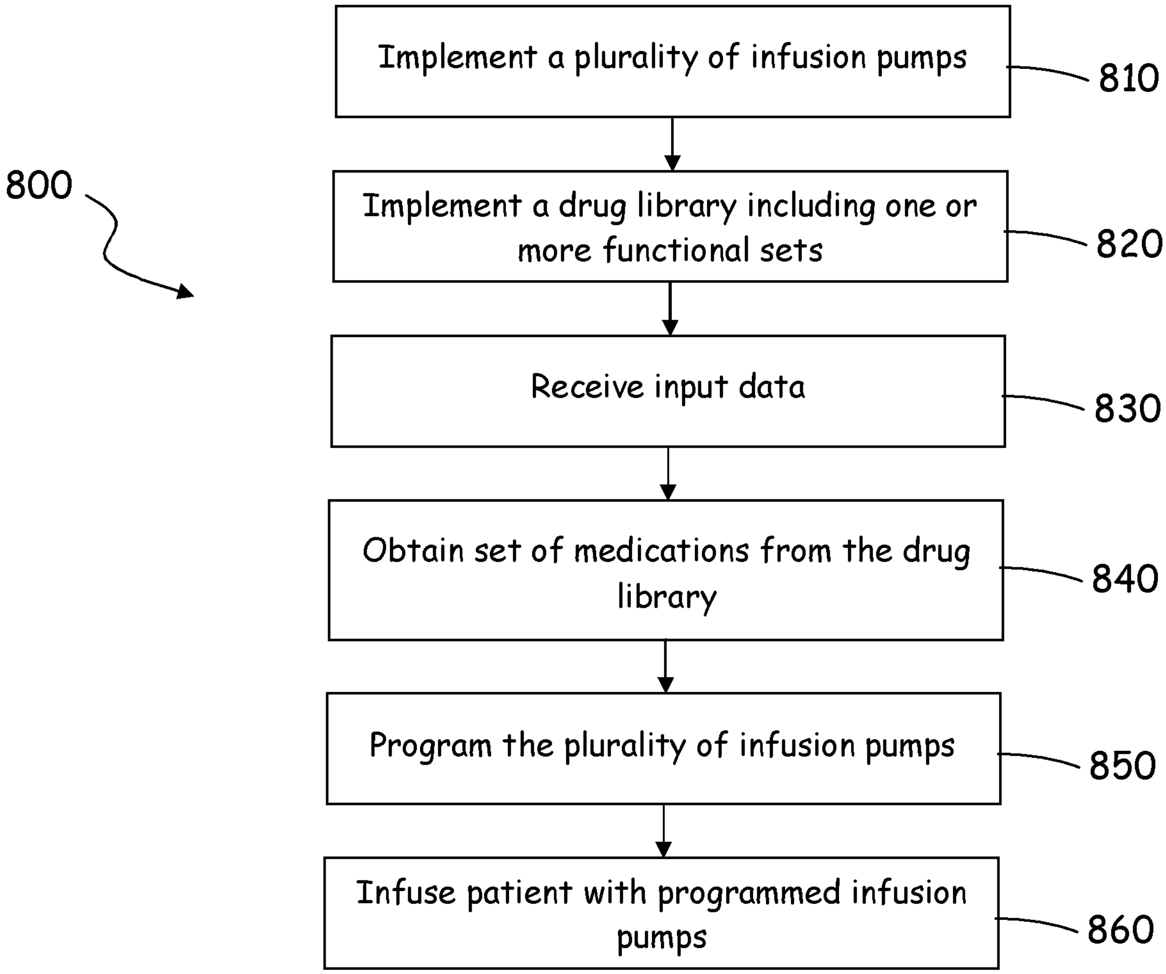
FIG. 8 is a flowchart of a method for procedure-based programming of a plurality of infusion pumps in a functional set, according to an embodiment.

Referring to FIG. 8, a flowchart of a method 800 for procedure-based programming of a plurality of infusion pumps in a functional set is depicted, according to an embodiment.

At 810, a plurality of infusion pumps are implemented. For example, each of the plurality of infusion pumps can be substantially similar to any of the infusion pumps described herein, such as infusion pump 210 as depicted in FIG. 2. In an embodiment, the plurality of infusion pumps can be activated, turned on, or otherwise prepared for operation. In embodiments, the plurality of infusion pumps are operably coupled to a patient. In another embodiment, the plurality of infusion pumps are staged for coupling to a patient.

At 820, a drug library including one or more functional sets is implemented. For example, the drug library can be substantially similar to any of the drug libraries described herein, such as the template of the portion of generic drug library 300 as depicted in FIG. 3. In an embodiment, implementing the drug library comprises receiving inputs that define the functional set and the corresponding set of medications to be infused. In embodiments, other inputs can define the number or type of infusion pumps needed or other criteria or fields related to the set of medications to be infused.

At 830, input data is received. In an embodiment, input data comprises a functional set selection. For example, referring to FIG. 6, procedure data 608 is input into programming engine 610 as the selected functional set. In other embodiments, input data further comprises hospital data, patient data, and/or sensor data. For example, referring again to FIG. 6, inputs such as hospital data 602, patient data 604, and sensor data 606 are input into programming engine 610. Input data can be received by manual input into the programming engine, such as on a pump or embedded server as aforementioned. In other embodiments, input data can be automatically transmitted to the programming engine.

Referring again to FIG. 8 at 840, a set of medications is obtained from the drug library implemented at 820. In an embodiment, the functional set selection corresponds to a set of medications in the drug library. In another embodiment, referring to FIG. 6, processor 620 evaluates received hospital data 602, patient data 604, sensor data 606, and procedure data 608 in view of drug library 618. As selected by procedure data 608, a set of medications to be infused is chosen. Processor 620 can then utilize drug library 618 in view of received hospital data 602, patient data 604, and sensor data 606 to select a particular set of medications specific for the unique combination defined by the received input data.

Referring again to FIG. 8 at 850, the plurality of infusion pumps are programmed according to the set of medications obtained from the drug library at 840. For example, again referring to FIG. 6, processor 620 transmits a programming signal to any of the plurality of infusion pumps, such as infusion pump 612, infusion pump 614, and infusion pump 616. In an embodiment, each of the infusion pumps receives a set of instructions that are part of the larger set of instructions. Each pump can then parse the received message for its particular protocol and delivery characteristics. In another embodiment, each pump is individually sent programming instructions or commands for its particular protocol and delivery characteristics such that parsing of a larger message is not needed. The pumps are then respectively programmed for operation according to the set of medications defined by the drug library.

Referring again to FIG. 8 at 860, the plurality of infusion pumps respectively infuse the patient according to the set of medications programmed at 850. In an embodiment, at 860, a clinician loads the drug container onto each of the plurality of pumps per its respective programmed setup configuration. The clinician can then verify the information is correct on each of the plurality of pumps. In an embodiment, the clinician can then start each pump to initiate their respective infusion processes.

Various embodiments of systems, devices, and methods have been described herein. These embodiments are given only by way of example and are not intended to limit the scope of subject matter hereof. It should be appreciated, moreover, that the various features of the embodiments that have been described may be combined in various ways to produce numerous additional embodiments. Moreover, while various materials, dimensions, shapes, configurations and locations, etc. have been described for use with disclosed embodiments, others besides those disclosed may be utilized commensurate with the scope of subject matter hereof.

Persons of ordinary skill in the relevant arts will recognize that subject matter hereof may comprise fewer features than illustrated in any individual embodiment described above. The embodiments described herein are not meant to be an exhaustive presentation of the ways in which the various features of subject matter hereof may be combined. Accordingly, the embodiments are not mutually exclusive combinations of features; rather, the subject matter hereof may comprise a combination of different individual features selected from different individual embodiments, as understood by persons of ordinary skill in the art.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims of subject matter hereof, it is expressly intended that the provisions of Section 112, sixth paragraph of 35 U.S.C. are not to be invoked unless the specific terms "means for" or "step for" are recited in a claim.

The invention claimed is:

1. A method of configuring a plurality of infusion pumps according to a functional set, the method comprising:
- implementing a plurality of infusion pumps, each of the infusion pumps configured to administer medication to a patient;
- implementing a drug library, the drug library including at least one functional set defining a set of medications;
- implementing a processor for receiving input data related to one of the at least one functional sets;
- obtaining a particular set of infusates from the drug library corresponding to the input data;
- configuring the processor for suggestion of a previously determined set of infusions or infusion parameters based at least in part on previously evaluated input data;
- programming the plurality of infusion pumps according to the set of infusates and the suggestion of a previously determined set of infusions or infusion parameters; and
- infusing the patient with the plurality of infusion pumps.

2. The method of configuring a plurality of infusion pumps according to a functional set of claim 1, wherein the previously evaluated input data further comprises at least one of hospital data, patient data, or sensor data, and obtaining the particular set of infusates from the drug library further comprises evaluating the at least one of hospital data, patient data, or sensor data.

3. The method of configuring a plurality of infusion pumps according to a functional set of claim 1, wherein programming the plurality of infusion pumps comprises programming each of the infusates in the set of infusates for infusion into one of the plurality of infusion pumps.

4. The method of configuring a plurality of infusion pumps according to a functional set of claim 1, further comprising communicatively coupling the plurality of infusion pumps such that the plurality of infusion pumps used in the functional set are associated with each other.

5. The method of configuring a plurality of infusion pumps according to a functional set of claim 4, wherein receiving input data comprises receiving user interface input at a first infusion pump, and wherein programming the plurality of infusion pumps comprises transmitting a command from the first infusion pump to the other of the plurality of infusion pumps.

6. The method of configuring a plurality of infusion pumps according to a functional set of claim 4, wherein receiving input data comprises receiving a command with a programming engine, and wherein programming the plurality of infusion pumps comprises transmitting a command from the programming engine to the plurality of infusion pumps.

7. The method of configuring a plurality of infusion pumps according to a functional set of claim 1, wherein the functional set comprises a hospital procedure.

8. The method of configuring a plurality of infusion pumps according to a functional set of claim 1, wherein the functional set defining a set of medications is set at a hospital network level, a hospital level, a department level, or a procedure level.

9. The method of configuring a plurality of infusion pumps according to a functional set of claim 1, wherein the drug library further comprises a plurality of sets of medications for each functional set.

10. A system for programming a plurality of infusion pumps, the system comprising:
- a plurality of infusion pumps, each of the infusion pumps configured to administer medication to a patient;
- an input source configured to receive a selected functional set;
- a programming engine including:
- a drug library including at least one functional set corresponding to the selected functional set defining a set of medications;
- a communications engine configured to interface to the plurality of infusion pumps and the input source;
- a processor configured (i) for suggestion of a previously determined set of infusions or infusion parameters based at least in part on previously evaluated input data and (ii) to interface to the drug library and to command the communications engine to program the plurality of infusion pumps according to the selected functional set and with reference to the suggestion of a previously determined set of infusions or infusion parameters.

11. The system for programming a plurality of infusion pumps of claim 10, wherein the input source is further configured to receive at least one of hospital data, patient data, or sensor data.

12. The system for programming a plurality of infusion pumps of claim 11, wherein the processor is further configured to evaluate the received at least one of hospital data, patient data, or sensor data to determine the set of medications.

13. The system for programming a plurality of infusion pumps of claim 10, wherein the input source is a user interface at a first infusion pump, and wherein the communications engine is configured to transmit a command from the first infusion pump to the other of the plurality of infusion pumps.

14. The system for programming a plurality of infusion pumps of claim 10, wherein the functional set comprises a hospital procedure.

15. The system for programming a plurality of infusion pumps of claim 10, wherein the functional set defining a set of medications is set at a hospital network level, a hospital level, a department level, or a procedure level.

* * * * *